United States Patent [19]

Lipkin

[11] Patent Number: 5,558,081
[45] Date of Patent: Sep. 24, 1996

[54] SURGICAL METHOD FOR INSERTING A TRANSTRACHEAL CATHETER

[76] Inventor: Alan Lipkin, 5410 E. Nassau Cir., Englewood, Colo. 80110

[21] Appl. No.: 596,719

[22] Filed: Feb. 5, 1996

Related U.S. Application Data

[63] Continuation-in-part of Ser. No. 521,025, Aug. 29, 1995, abandoned.

[51] Int. Cl.⁶ .................................................. A61M 15/00
[52] U.S. Cl. .............................. 128/200.24; 128/207.29; 128/200.26; 128/207.14
[58] Field of Search ....................... 128/200.24, 200.26, 128/207.14, 207.15, 207.29

[56] References Cited

U.S. PATENT DOCUMENTS

| | | | |
|---|---|---|---|
| 3,307,551 | 3/1967 | Violet, Jr. | 128/207.29 |
| 4,608,982 | 9/1986 | Pollard | 606/190 |
| 4,677,978 | 7/1987 | Melker | 128/207.14 |
| 4,889,112 | 12/1989 | Schachner et al. | 128/200.26 |
| 5,186,168 | 2/1993 | Spofford et al. | 128/207.29 |
| 5,279,285 | 1/1994 | Griggs | 128/200.26 |
| 5,339,809 | 8/1994 | Beck, Jr. et al. | 128/207.29 |

OTHER PUBLICATIONS

Dorland's Illustrated Medical Dictionary, 27th ed., 1988, pp. 1072, 1076, 1534.
Stedman's Medical Dictionary, 25th ed., 1990, pp. 993, 999.
Anatomy of the Human Body, Gray et al., 13th ed., 1985, pp. 458–461.

*Primary Examiner*—Aaron J. Lewis
*Attorney, Agent, or Firm*—Dorr, Carson, Sloan & Birney, P.C.

[57] ABSTRACT

A surgical procedure for creating a saucerized tract for insertion of a transtracheal catheter allows early institution of transtracheal oxygen therapy, facilitates rapid tract maturation, and reduces the incidence of post-operative complications. A vertical incision is made through the skin and subcutaneous tissue at the midline of the patient's neck overlying the trachea, and the sternothyroid muscle is dissected apart to expose the trachea. Local advancement flaps, preferably consisting of full-thickness skin, are elevated on either side of the incision, and subcutaneous fat is removed from beneath the incision and flaps. The flaps are then tunneled toward the trachea and sutured to the undersides of the separated sternothyroid muscle to form a saucerized region. An opening is created through the trachea within the saucerized region and a temporary stent is inserted. After a brief initial healing period of about one day, the stent can be removed and replaced with a transtracheal catheter. In the preferred embodiment, the stent is a tracheostomy tube having a flexible cuff that substantially fills the saucerized region.

15 Claims, 5 Drawing Sheets

SURGICAL METHOD FOR INSERTING A TRANSTRACHEAL CATHETER

RELATED APPLICATION

The present application is a continuation-in-part of the Applicant's U.S. patent application Ser. No. 08/521,025, entitled "Surgical Method for Inserting a Transtracheal Catheter", filed on Aug. 29, 1995 now abandoned.

BACKGROUND OF THE INVENTION

1. Field of the Invention

The present invention relates generally to the field of transtracheal catheters. More specifically, the present invention discloses a surgical method for inserting a transtracheal catheter into the trachea of a patient.

2. Statement of the Problem

Various types of transtracheal catheters have been widely used in the medical field for many years to provide oxygen therapy to cardiac and pulmonary patients. The most common method for inserting a transtracheal catheter is known as the modified Seldinger technique. Under local anesthesia, a hypodermic needle is passed through the anterior neck into the trachea. A guide wire is inserted through the needle into the trachea. The needle is then removed, leaving the guide wire in place. The size of the opening is progressively increased by inserting a dilator and then a non-functioning stent over the guide wire. The stent generally remains in place for at least one week to allow a degree of healing of the resulting tract. The stent is then withdrawn over the guide wire, a transtracheal catheter is inserted into the trachea, and transtracheal oxygen therapy is commenced.

Although the modified Seldinger technique is relatively simple, complications such as subcutaneous emphysema and pneumothorax have been known to occur. Few pulmonologists perform the procedure with sufficient frequency to obtain a high level of comfort and proficiency. In addition, this technique generally takes six to eight weeks for the tract to mature sufficiently to allow daily catheter changes and cleaning by the patient. Mucus balls can accumulate at the catheter tip during this period, which can lead to potentially dangerous episodes of upper airway obstruction. This is also the period when inadvertent catheter dislodgement is most likely to occur. Although transtracheal oxygen therapy can be administered through an immature tract, this requires a detailed and laborious protocol for tract maintenance and catheter cleaning that cannot typically be done by the patient without professional assistance. These concerns mandate that out-of-town patients must remain relatively close to a major medical center during this period.

Once the tract matures, there is still a significant incidence of tract-related complications. Tract granulations and keloids can lead to pain and bleeding. Approximately 7% to 15% of patients develop tracheal chondritis, which may become a chronic problem. Inadvertent catheter dislodgement can occur even with a mature tract, and occurs in about 22% to 35% of all patients on transtracheal oxygen therapy at some point. This leads to an emergency office or hospital visit for reinsertion, which can be both uncomfortable and painful. Complete closure of the epithelial tract occurs in about 7% to 10% of patients.

The following are other examples of the prior art relating to procedures or devices for inserting transtracheal catheters or performing tracheostomies:

| Inventor | Patent No. | Issue Date |
| --- | --- | --- |
| Violet | 3,307,551 | March 7, 1967 |
| Pollard | 4,608,982 | Sept. 2, 1986 |
| Melker | 4,677,978 | July 7, 1987 |
| Schachner et al. | 4,889,112 | Dec. 26, 1989 |
| Spofford et al. | 5,186,168 | Feb. 16, 1993 |
| Griggs | 5,279,285 | Jan. 18, 1994 |
| Beck et al. | 5,339,809 | Aug. 23, 1994 |

Violet discloses an emergency tracheostomy kit that includes both a scalpel blade 16 and a tubular airway 18 that can be inserted into the incision.

Pollard discloses a surgical forceps for use in association with a catheter. The catheter can be used, for example, to puncture the wall of the trachea. Pollard also mentions that a conventional procedure is to excise the overlaying layers of skin and fat and then puncture the exposed muscle layer to reach the trachea. One example is shown in FIGS. 4 and 5 of the Pollard patent for the pleural cavity 30 instead of the trachea.

Melker discloses a system for performing emergency cricothyrotomy ventilation. A scalpel 12 is used to make the initial incision between the thyroid and cricoid cartilage.

Schachner et al. disclose an apparatus for performing a tracheostomy operation. The trachea is initially penetrated using a syringe needle. A guide wire is then inserted through the small opening in the trachea. The instrument (T) is inserted into the opening while being guided by the wire. The instrument is opened after insertion to widen the trachea opening and allow subsequent insertion of a cannula.

Spofford et al. disclose a transtracheal catheter system. This patent discloses a method of insertion using a hypodermic needle to initially insert a guide wire into the trachea. A dilator is then inserted over the guide wire to form a tract. A temporary stent is used to maintain the opening during an initial healing period before the transtracheal catheter is inserted.

Griggs discloses another example of a method and apparatus for inserting a tracheostomy tube into the trachea of a patient. Here again, a hollow needle is used to make the initial opening into the trachea.

Beck et al. disclose another method for providing oxygen therapy using a cricothyroidal endotracheal device.

3. Solution to the Problem

None of the prior art references use the present surgical procedure of creating skin flaps at the edges of the incision, removing subcutaneous fat, and suturing the flaps to the sternothyroid muscle to create a saucerized tract for insertion of a transtracheal catheter. In addition, none of the prior art references combine the present surgical technique with use of a tracheostomy tube as a stent during initial healing of the tract.

SUMMARY OF THE INVENTION

This invention provides a surgical procedure for insertion of a transtracheal catheter that allows early institution of transtracheal oxygen therapy, facilitates rapid tract maturation, and reduces the incidence of post-operative complications. A vertical incision is made through the patient's skin and subcutaneous tissue at the midline of the patient's neck overlying the trachea, and the sternothyroid muscle is dissected apart to expose the trachea. Local advancement flaps, preferably consisting of full-thickness skin, are elevated on either side of the incision, and subcutaneous fat is removed from beneath the incision and flaps. The flaps are then tunneled toward the trachea and sutured to the undersides of the separated sternothyroid muscle to form a saucerized region. An opening is creating through the trachea within the saucerized region and a temporary stent is inserted. After a brief initial healing period of about one day, the stent can be removed and replaced with a transtracheal catheter. In the preferred embodiment, the stent is a tracheostomy tube having a flexible cuff that substantially fills the saucerized region.

A primary object of the present invention is to provide a surgical procedure for inserting transtracheal catheters that allows early institution of transtracheal oxygen therapy and facilitates rapid tract maturation.

Another object of the present invention is to provide a surgical procedure for inserting transtracheal catheters that substantially reduces the incidence of post-operative complications, such as mucus balls, lost tracts, and tracheal chondritis.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Surgical Procedure

The procedure is generally performed in the hospital operating room under local anesthesia with intravenous sedation and continuous monitoring by an anesthesiologist. The potential site for catheter insertion is marked by the physician prior to the procedure. A roll is placed under the patient's shoulders to permit neck extension, and the area between the cricoid and sternal notch is infiltrated with a local anesthetic (e.g., lidocaine 2% with epinephrine 1:100,000).

Figure 1:
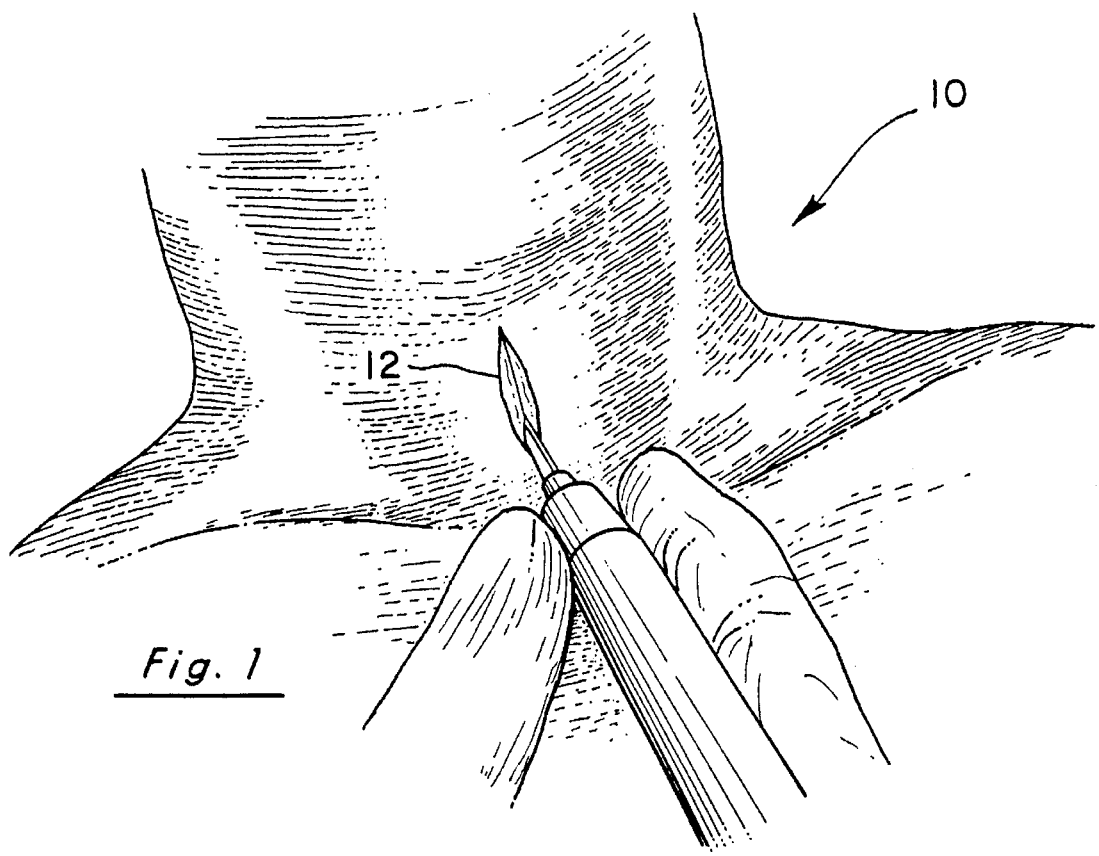
FIG. 1 is a front view of the patient's neck 10 as the initial incision 12 is made.
Figure 2:
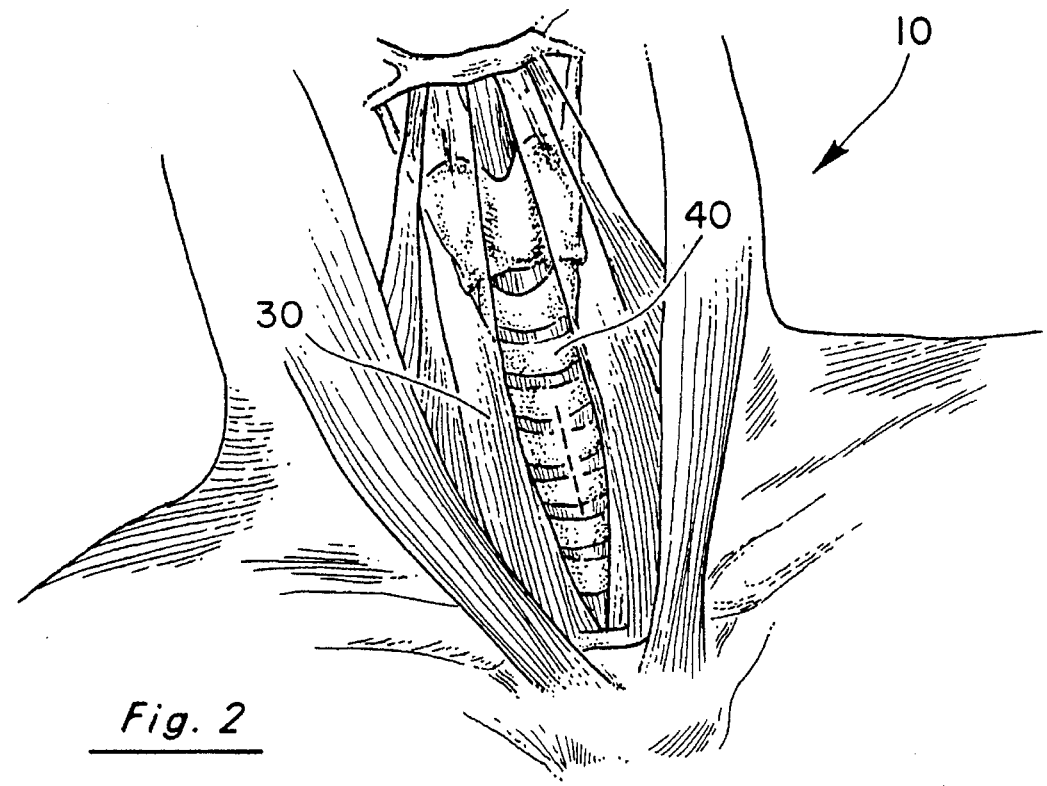
FIG. 2 is a front cut-away view generally showing the anatomy of the anterior portion of the neck.
Figure 3:
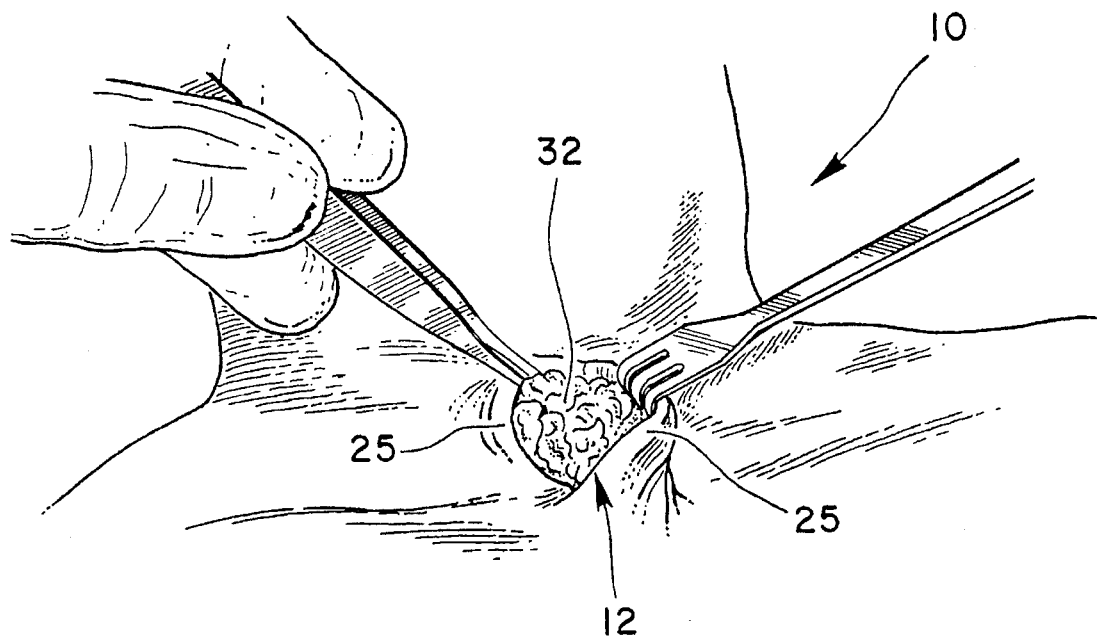
FIG. 3 is a front view of the patient's neck 10 showing removal of subcutaneous fat 35 from the incision 12.
Figure 4:
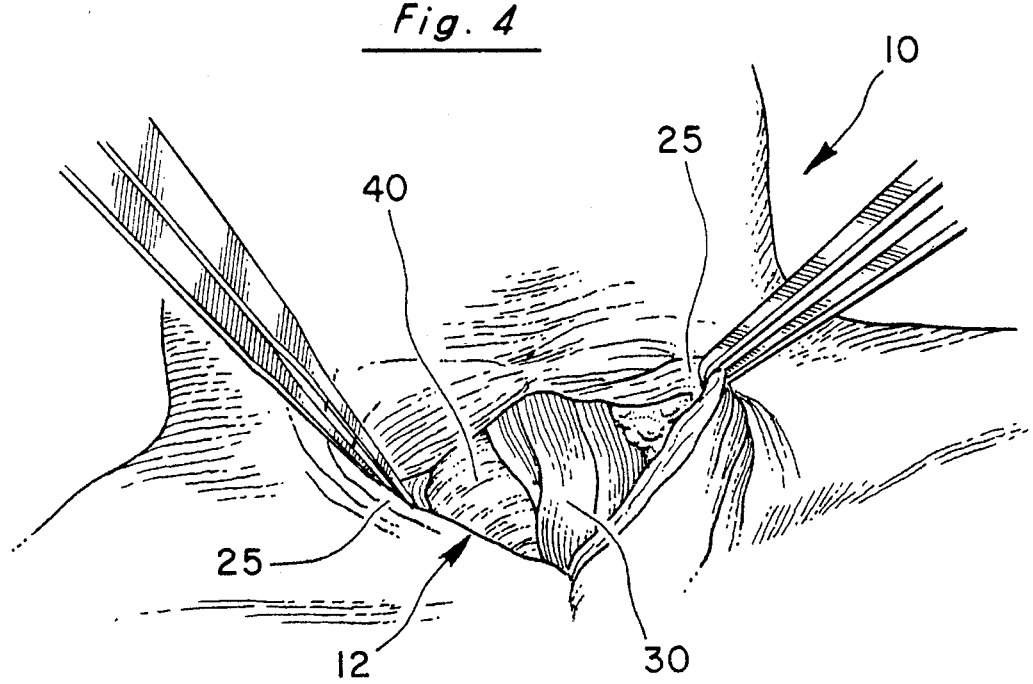
FIG. 4 is a front view of the patient's neck 10 after the sternothyroid muscle 30 has been dissected apart to expose the trachea 40 and local advancement flaps 25 have been raised laterally to either side of the incision 12.
Figure 5:
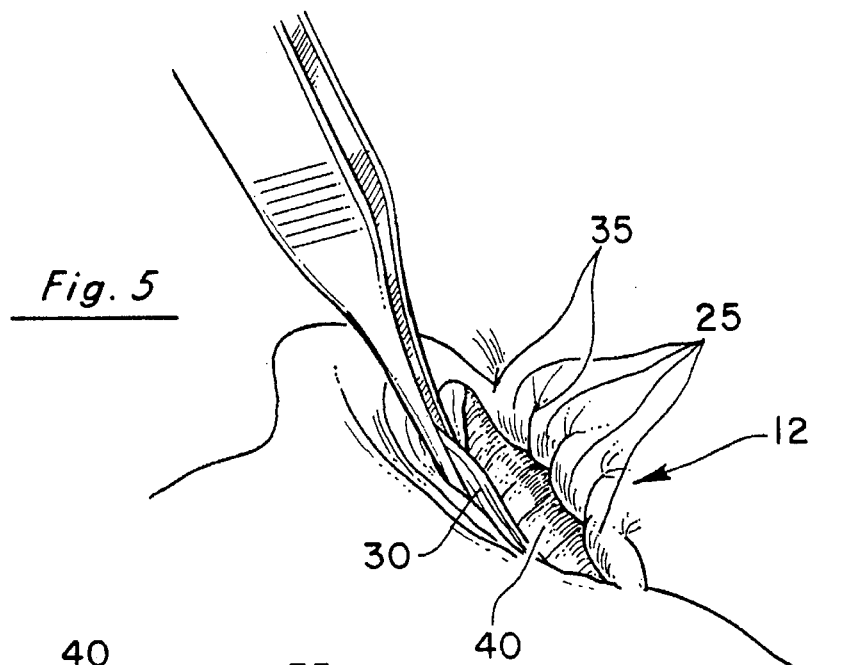
FIG. 5 is a front view of the incision 12 as the flaps 25 are sutured to the underside of the sternothyroid muscle.

FIG. 2 generally shows the anatomy of the anterior neck for general reference. After sterile preparation and draping, a vertical incision 12 with a length of approximately 1 cm to 2 cm is made at the midline of the patient's neck 10 with a cutting cautery or a surgical blade, as shown in FIG. 1. In the preferred embodiment, the incision is made in the region overlying tracheal rings two, three, and four. Local advancement flaps 25, preferably consisting of full-thickness skin, are raised lateral to either side of the incision 12 as illustrated in FIGS. 3 and 4. The length of the flaps depends on the distance from the skin to the trachea, but averages about 2 cm. Subcutaneous fat 32 is removed beneath the incision 12 and flaps 25 all the way down to the sternothyroid muscle 30. This cervical lipectomy decreases the distance between the skin and trachea 40, lengthens the epithelialized tract, and saucerizes it. The sternothyroid muscle 30 are dissected apart at the midline, down to the trachea 40. This is shown most clearly in FIG. 4. The thyroid isthmus is retracted superiorly or divided as necessary. The flaps 25 are then tunneled toward the trachea 40 and are sutured 35 to the undersides of the separated sternothyroid muscle 30, as shown in FIG. 5. For example, this can be performed with a running suture of 3-0 Vicryl and may be reinforced with additional interrupted sutures as necessary. Lidocaine 1% without epinephrine is instilled transtracheally to anesthetize the tracheal mucosa.

Figure 6:
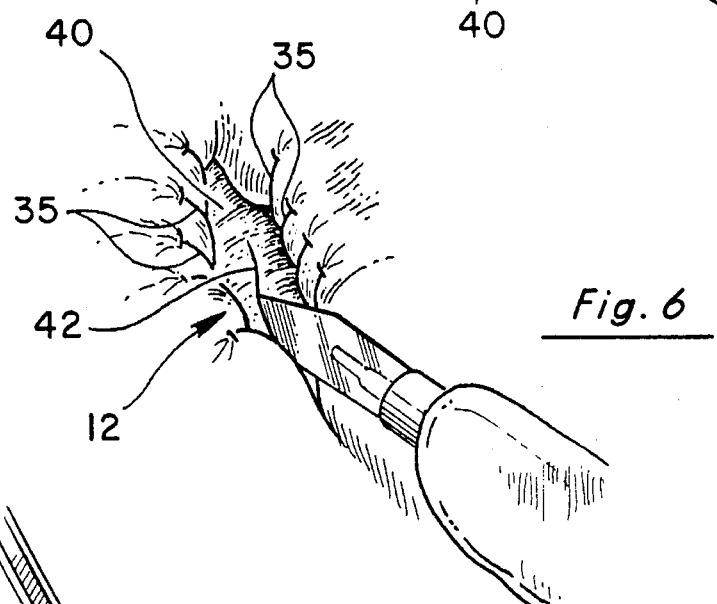
FIG. 6 is a front view of the incision 12 as an initial opening 42 is cut into the tracheal cartilage 40 with a surgical blade.
Figure 7:
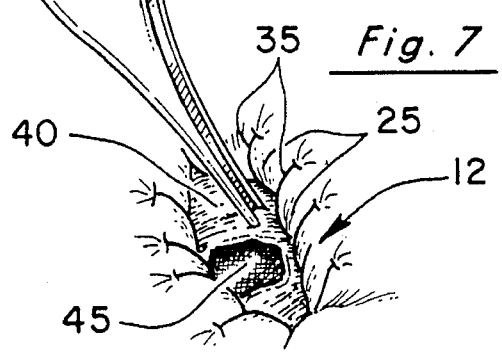
FIG. 7 is a front view of the incision 12 as a tracheal cartilage is resected to form a window 45.
Figure 8:
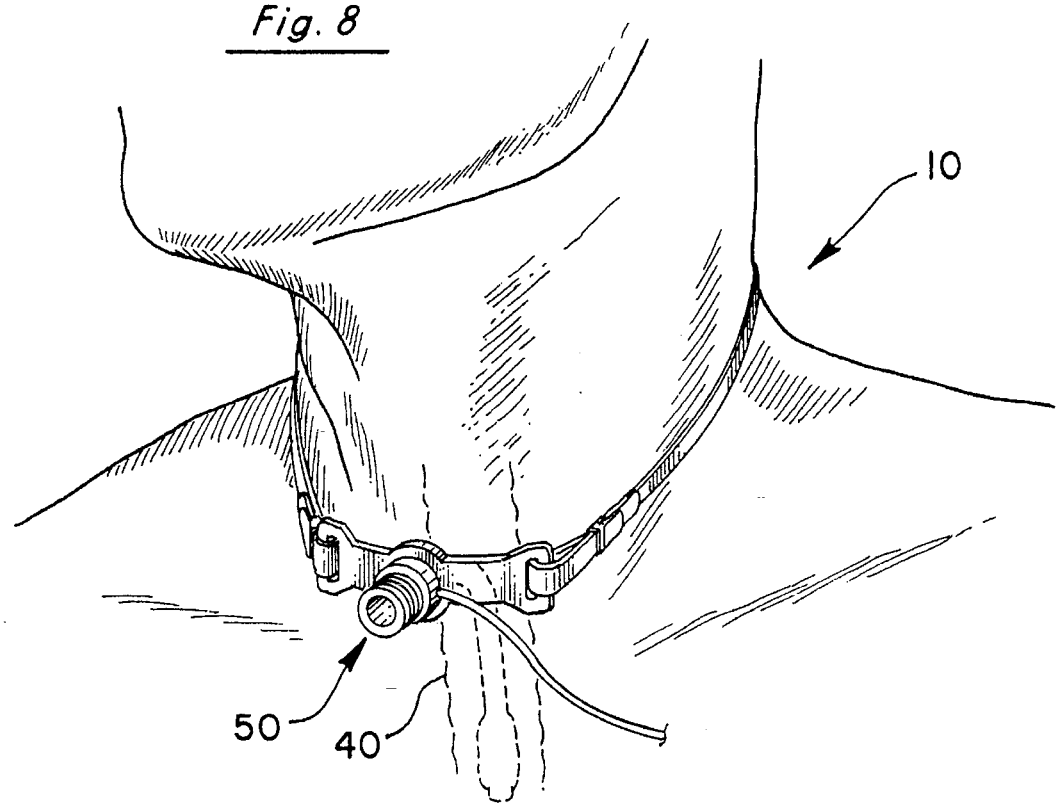
FIG. 8 is a front view of the patient's neck after insertion of a tracheostomy tube 50 as a temporary stent.

The trachea is then opened at the level of the second ring. This can be performed freehand with a #11 blade, as depicted in FIG. 6, or with a modified cardiac punch. The initial opening 42 is enlarged to create a window 45 by resecting a portion of the tracheal cartilage 40, as shown in FIG. 7. In the preferred embodiment, the window 45 is just large enough to accommodate a #4 tracheostomy tube or other stent. For example, a window diameter of approximately 6.25 mm is sufficient for a stent having a 6 mm diameter. The sutured flaps 25 and the exposed area of trachea cartilage form a saucerized region surrounding the window 45. Due to the high oxygen concentration in the patient's airway, the cautery should no longer be used after the trachea 40 is opened. The stent 50 is inserted and secured, as shown in FIG. 8, and the patient is escorted to the recovery room.

Stent

Figure 9:
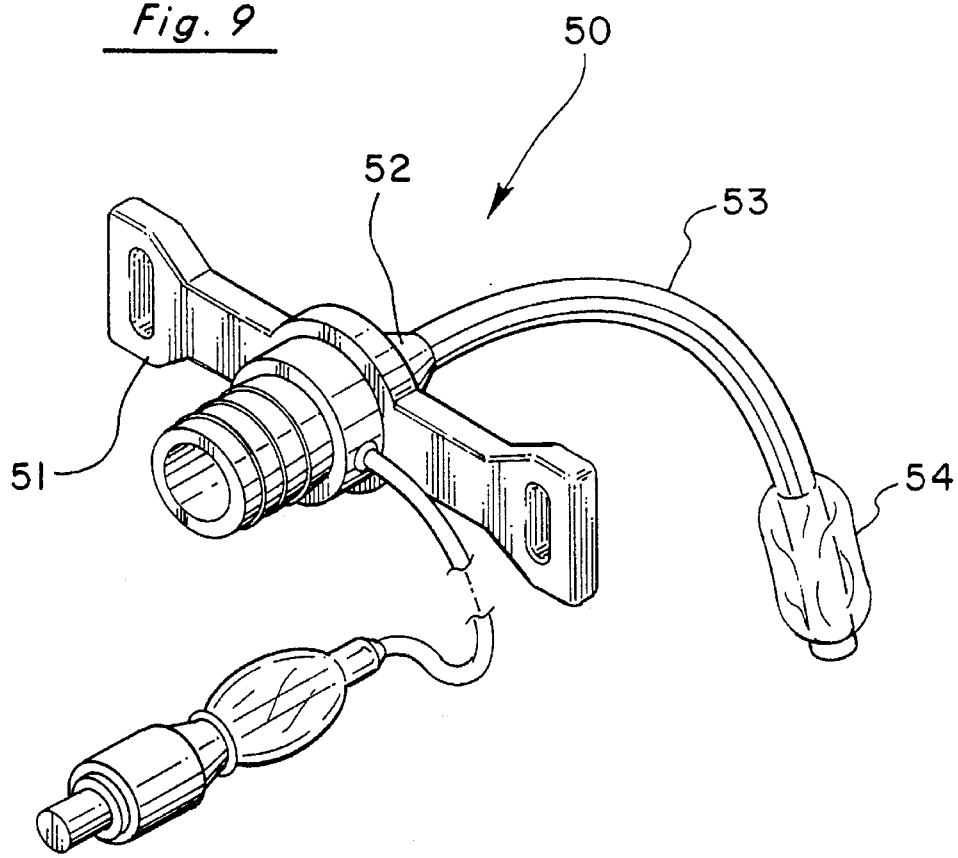
FIG. 9 is a front perspective view of the tracheostomy tube 50.
Figure 10:
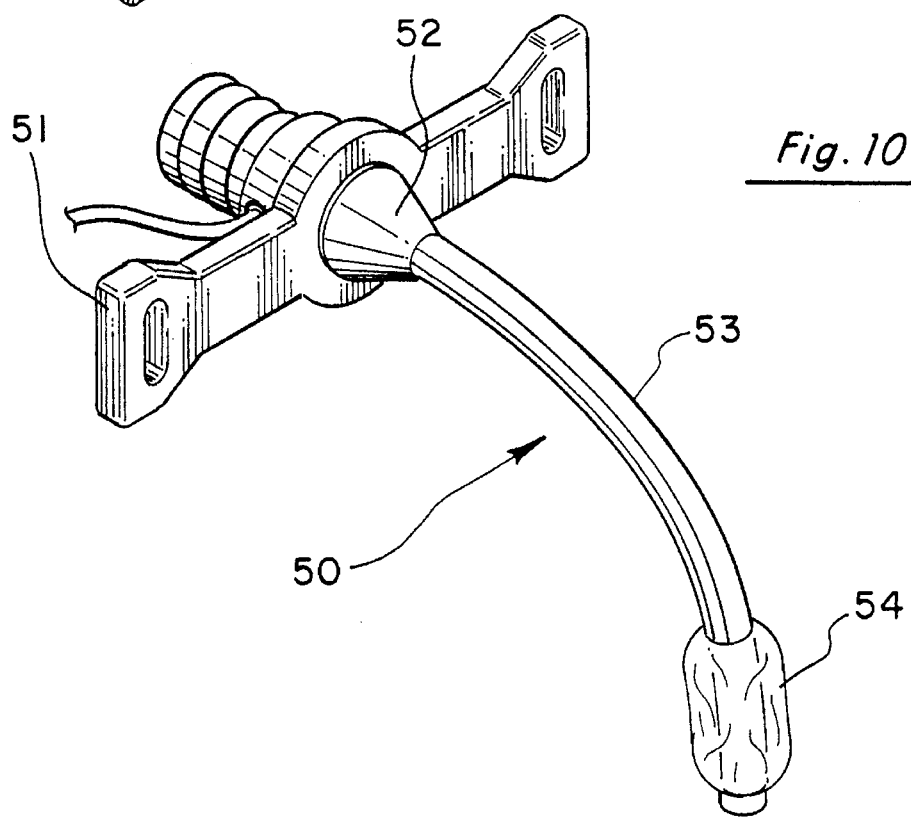
FIG. 10 is a rear perspective view of the tracheostomy tube 50.

In the preferred embodiment, a tracheostomy tube is used as the stent 50. For example, a line of flexible tracheostomy tubes made of silicone are marketed by Bivona Medical Technologies of Gary, Ind. FIGS. 9 and 10 illustrate a Bivona tracheostomy tube having a tubular portion 53 for insertion through the window 45 in the trachea 40, a neck flange 51, and a flexible annular cuff 52 surrounding the tubular portion 53 of the tracheostomy tube 50 adjacent to the neck flange 51. The cuff 52 substantially fills the saucerized region surrounding the tract. The cuff 52 keeps the saucerized tract open, eliminates hematoma formation, decreases soft tissue swelling, and facilitates rapid post-operative conversion to the transtracheal catheter. The Bivona tracheostomy tube has an intratracheal length of 11 cm that is identical to the length of a standard transtracheal catheter. Thus, a post-operative chest x-ray enables the physician to determine whether the patient will need a transtracheal catheter with a standard or modified length. The inflatable cuff 54 at the distal end of tracheostomy tube 50 can be inflated and the patient can be attached to a mechanical ventilation system via the tracheostomy tube 50, if needed on an emergency basis. The cuff 54 can be inflated to fully and symmetrically occlude the remainder of the tracheal lumen to allow emergency ventilation through the tracheostomy tube 50. The cuff 54 can be deflated sufficiently to allow unrestricted breathing around the tracheostomy tube 50 at other times.

Post-Operative Care

Figure 11:
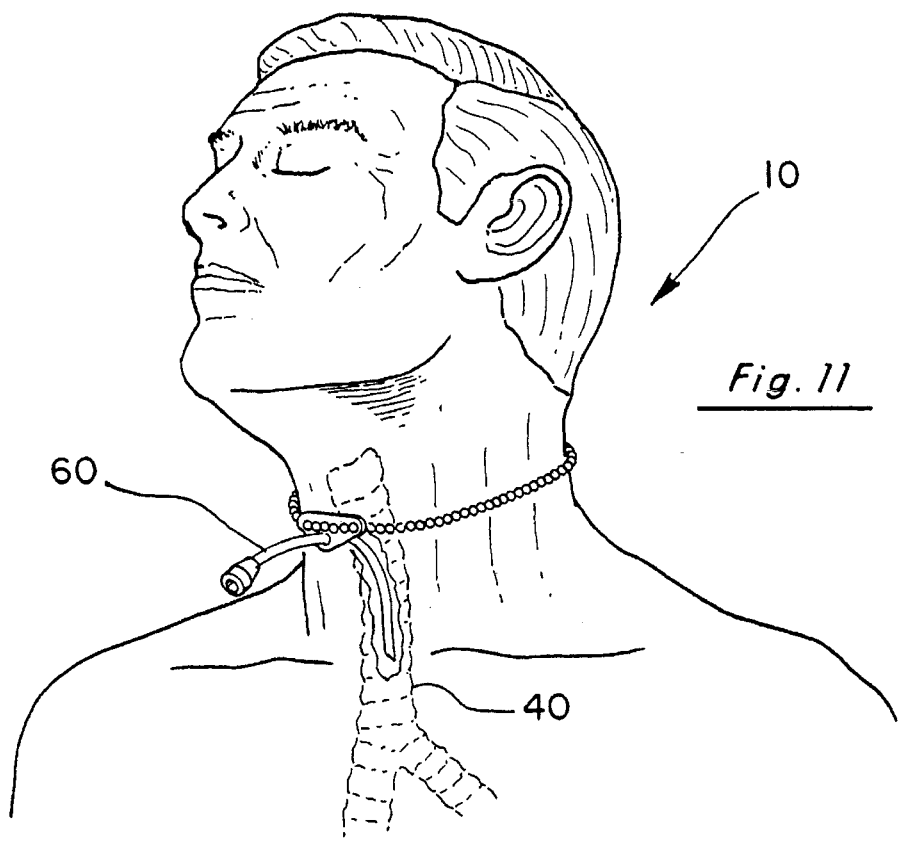
FIG. 11 is a perspective view of the patient's head and neck after the stent has been removed and a transtracheal catheter 60 has been inserted into the trachea 40.

The patient is observed overnight in the hospital. Humidified oxygen flow via the tracheostomy tube is titrated to keep blood oxygen saturation at appropriate levels. Guaifenesin can be administered orally as a mucolytic (1200 mg every 12 hours). Benzonatate is administered orally for cough suppression (200 mg every 8 hours), and xylocaine (1% liquid, 1 or 2 cc) may be instilled via the tracheostomy tube every 3 to 4 hours for additional analgesia and cough suppression. Prophylactic cephalexin (250 mg) is given orally every 6 hours. Narcotic analgesics can be administered judiciously, keeping in mind the potential for additional respiratory suppression in this group of patients having respiratory systems that are already compromised. On the first post-operative morning, the stent 50 can be removed over a wire, and a transtracheal catheter 60 (e.g., SCOOP-1™, Transtracheal Systems, Inc., Englewood, Colo.) inserted into the patient's trachea 40 through the tract, as illustrated in FIG. 11. The patient can then be discharged, either to home or to a long-term care facility for a more complete program of pulmonary rehabilitation. During the period of tract maturation, the patient is instructed in local care and the procedures necessary for changing the transtracheal catheter 60.

Clinical Study

The applicant has conducted a clinical study in which 34 patients underwent the surgical procedure discussed above for inserting a transtracheal catheter. Some of the initial cases were revisions of unusable tracts that had been created with the modified Seldinger technique, but the more recent cases employed only the present surgical procedure. These patients were compared to 66 patients who had undergone the modified Seldinger technique. The present procedure was generally well tolerated, with no significant perioperative complications in a group of patients having numerous pre-existing medical problems.

All of the patients were able to commence transtracheal oxygen therapy via a SCOOP™ transtracheal catheter on the first post-operative day. In contrast, patients undergoing the modified Seldinger technique waited at least one week before being able to make use of the newly created tract.

Patients were also able to progress more rapidly to the point of having a mature tract, with the patient being able to remove and reinsert the SCOOP™ transtracheal catheter on a twice-daily basis. Patients undergoing the modified Seldinger technique required an average of 56 days to reach this point, in contrast to an average of 14 days for patients undergoing the present procedure.

Post-operative complications were greatly reduced. There were no inadvertent tract losses, in contrast to a 30% rate of lost tracts among patients undergoing the modified Seldinger technique. The incidence of chondritis was reduced from 25% to 11%, and the incidence of mucus balls was reduced from 44% to 3%.

To summarize, the present procedure allows early institution of transtracheal oxygen therapy, facilitates rapid tract maturation, and reduces the incidence of problems related to mucus balls, lost tracts, and chondritis. It is well tolerated by patients and is useful as both a primary method of tract creation and a revision procedure for tract problems encountered with the modified Seldinger technique.

The above disclosure sets forth a number of embodiments of the present invention. Other arrangements or embodiments, not precisely set forth, could be practiced under the teachings of the present invention and as set forth in the following claims.

I claim:

1. A method for inserting a transtracheal catheter into a patient's trachea said method comprising:

making an incision through the patient's skin and subcutaneous tissue at a midline of the patient's neck overlying the trachea;

dissecting the patient's sternothyroid muscle apart within the incision to expose said trachea;

creating local advancement flaps on either side of the incision;

removing subcutaneous fat from beneath the flaps;

suturing the flaps to the sternothyroid muscle within the incision;

creating an opening through the trachea within the area exposed by the incision; and inserting a transtracheal catheter through the opening into the trachea.

2. The method of claim 1 further comprising:

suturing the local advancement to an underside of the sternothyroid muscle.

3. The method of claim 1 further comprising:

making the incision a vertical incision at the midline of the patient's neck in the area of tracheal rings two, three, and four.

4. The method of claim 3 further comprising:

making the incision a length of approximately 1 cm to 2 cm.

5. The method of claim 1 further comprising:

making the local advancement flaps a length of approximately 2 cm.

6. The method of claim 1 further comprising the step of inserting a temporary stent through the opening into the trachea for an initial healing period prior to insertion of a transtracheal catheter.

7. The method of claim 6 further comprising:

providing a stent
a tubular potion for insertion through the opening;
a neck flange extending from the tubular potion; and
a cuff surrounding the tubular potion adjacent to the neck flange.

8. The method of claim 6 further comprising:

inserting a temporary stent for approximately one day, removing the stent after one day and subsequently inserting a transtracheal catheter.

9. The method of claim 6 further comprising:

providing a stent which is a tracheostomy tube.

10. A method for inserting a transtracheal catheter into a patient's trachea, said method comprising:

making an incision through the patient's skin and subcutaneous tissue at a midline of the patient's neck overlying the trachea;

dissecting the patient's sternothyroid muscle apart within the incision to expose the trachea;

creating local advancement flaps on either side of the incision;

removing subcutaneous fat from beneath the flaps;

suturing the flaps to the sternothyroid muscle within the incision to form a saucerized region around the incision;

creating an opening through the trachea within the saucerized region;

inserting said temporary stent into the opening;

removing a stent after an initial healing period; and inserting a transtracheal catheter through the opening into the trachea.

11. The method of claim 10 further comprising:

suturing the flaps to an underside of the sternothyroid muscle.

12. The method of claim 10 further comprising:

providing a temporary stent having
- a tubular potion for insertion through the opening;
- a neck flange extending from the tubular potion; and
- a cuff surrounding said tubular potion adjacent to the neck flange that substantially fills the saucerized region around the opening.

13. The method of claim 10 further comprising:

inserting said temporary stent for approximately one day.

14. The method of claim 10 further comprising:

providing a temporary stent which comprises a tracheostomy tube.

15. A method for inserting a transtracheal catheter into a patient's trachea said method comprising:

making an incision through the patient's skin and subcutaneous tissue at a midline of the patient's neck overlying the trachea;

dissecting the patient's sternothyroid muscle apart within the incision to expose the trachea;

creating local advancement flaps on either side of the incision;

removing subcutaneous fat from beneath the flaps;

suturing the flaps to an underside of the sternothyroid muscle within the incision to form a saucerized region around the incision;

creating an opening through the trachea within the saucerized region;

temporarily inserting a tracheostomy tube into the opening, said tracheostomy tube having a flexible cuff that substantially fills the saucerized region;

removing a tracheostomy tube after an initial healing period; and inserting a transtracheal catheter through the opening into the trachea.

* * * * *